(12) United States Patent
Duncan et al.

(10) Patent No.: US 6,551,583 B2
(45) Date of Patent: Apr. 22, 2003

(54) ANTIBIOFOULING METHOD AND APPARATUS FOR OPTICAL SENSORS

(75) Inventors: Paul G. Duncan, Vienna, VA (US); Sean Michael Christian, Woodbridge, VA (US); David M. Orcutt, Blacksburg, VA (US)

(73) Assignee: Airak, Inc,, Manassas, VA (US)

( * ) Notice: Subject to any disclaimer, the term of this patent is extended or adjusted under 35 U.S.C. 154(b) by 0 days.

(21) Appl. No.: 09/841,163

(22) Filed: Apr. 25, 2001

(65) Prior Publication Data

US 2002/0044954 A1 Apr. 18, 2002

Related U.S. Application Data

(60) Provisional application No. 60/199,347, filed on Apr. 25, 2000, and provisional application No. 60/199,346, filed on Apr. 25, 2000.

(51) Int. Cl.$^7$ .................................................. A61L 9/01
(52) U.S. Cl. ...................... 424/76.8; 424/400; 424/76.1; 424/405; 424/409; 514/241; 514/254.07; 514/396
(58) Field of Search .................. 424/400, 484, 424/486, 76.1, 76.8, 405, 409; 514/241, 254.07, 396

(56) References Cited

U.S. PATENT DOCUMENTS 5,869,272 A    2/1999    Bogart et al. ............... 435/7.32

Primary Examiner—Michael G. Hartley
Assistant Examiner—Konata M. George
(74) Attorney, Agent, or Firm—Greenberg Traurig; Richard E. Kurtz, II

(57) ABSTRACT

An antibiofouling material, a method for making said antibiofouling material, a sensor apparatus employing said antibiofouling material, and a method of making said sensor apparatus. The disclosed antibiofouling material includes one or more biocides and one or more charge transfer compounds are embedded within a copolymer host matrix. Biocides used in the present invention may include, but are not limited to, Halobenzonitriles, Azoles, diuron; and simazine. Among its uses, the antibiofouling material of the present invention can be used in a sensor apparatus. In a preferred embodiment, one or more surfaces of said sensor apparatus are coated with an antibiofouling material comprised of one or more biocides, one or more charge transfer compounds, and a copolymer host matrix.

7 Claims, 11 Drawing Sheets

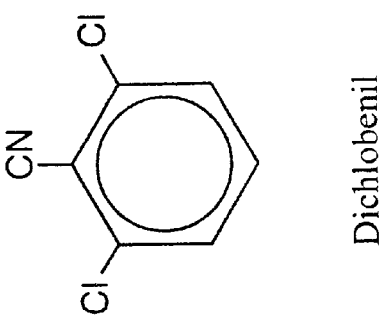
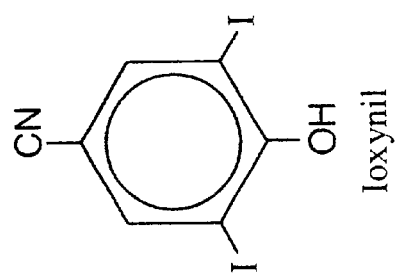
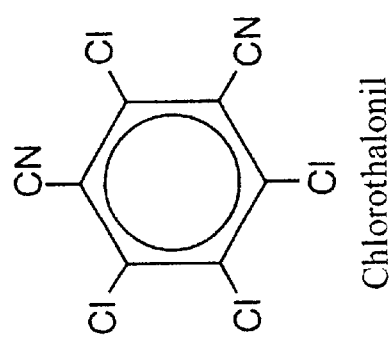
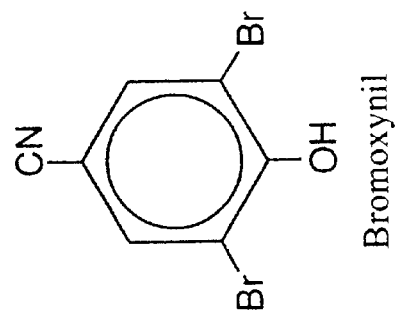
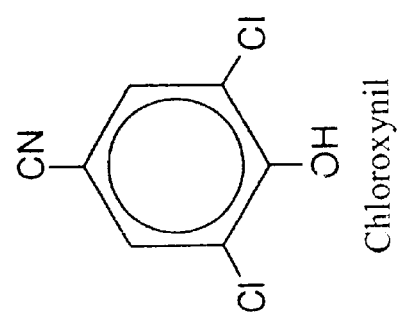
Figure 1

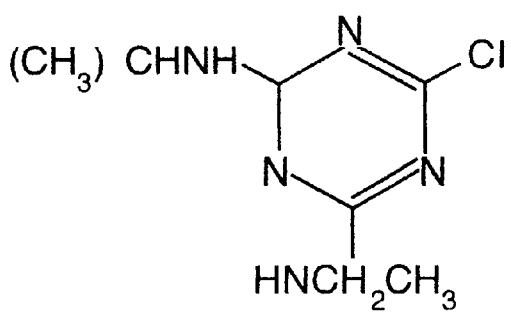
Atrazine
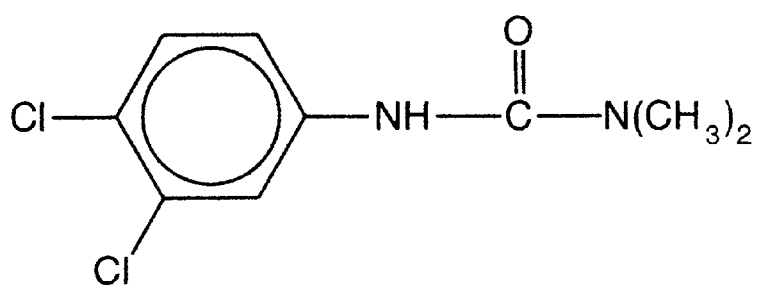
Diuron
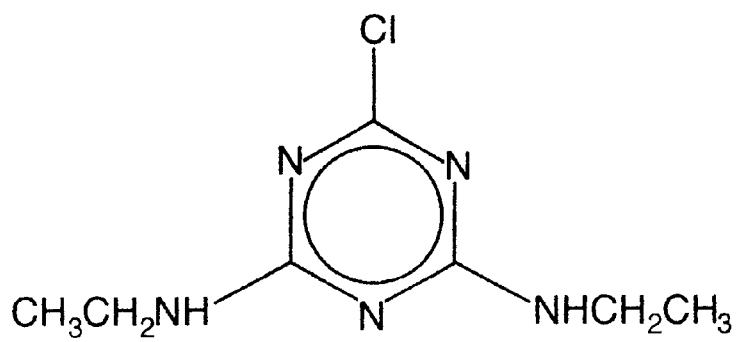
Simazine
*Figure 3*

HERBICIDES

Aliphatic Acids, Substituted Fatty Acids

Aromatic Acids, Including Alachlor and Metolachlor

Benzonitriles, Including Bromoxynil

Carbamates

Dinitroanilines, Including Trifluralin

Diphenylethers

Phenols

Phenoxyalkynoic Acids, Including 2,4-D; 2,4-DB; Mecoprop; and 2,4,5-T

Thiocarbamates, Including EPTC and Triallate

Triazines, Including Atrazine and Simazine

Uracils

Ureas, Including Diuron and Linuron

Miscellaneous, Including Glyphosate and Picloram

FUNGICIDES

Alanine Derivatives

Amides, Including Thiram

Carbamates, Including Benomyl

Chlorobenzenes

Imidazoles

Phophrothioates

Quinones

Triazoles

Miscellaneous, Including Captan, Chlorothalonil, and Folpet

*Figure 4*

4'4-Bis(dimethylamino)benzophenone
Poly(1,4-butanediol adipate)

Poly(2-chloro-1,3-butadiene)

Poly(2-hydroxypropyl methacrylate)
Poly siloxanes
Poly(4-aminostyrene)
Poly(4-hydroxybenzoic acid)
Poly(acrylamide/acrylic acid)
Poly(benzyl methacrylate)
Poly(dimethylsiloxane)
Poly(ethyl acrylate)
Poly(ethylene oxide)

Poly(hexamethylenesebacamide)
Poly(l-lactic acid)
Poly(methyl methacrylate)
Poly(N-vinylcarbazole)

Poly(tetrafluoroethylene)

Poly(vinyl alcohol), N-methyl-4(4'-formylstyryl)pyridinium methosulfate acetal
Poly(vinyl cinnamate)
Poly[methylene(polyphenyl) isocyanate]
Polyacrylamide
Polycaprolactone
Polyisobutylene
Polypyrrole Cellulose
Poly(1-glycerol methacrylate)

Poly(2-ethyl-2-oxazoline)

Poly(2-vinylpyridine N-oxide)
Poly(3-methylthiophene)
Poly(4-bromostyrene)
Poly(4-vinylphenol)
Poly(acrylic acid)
Poly(bisphenol A carbonate)
Poly(dl-lactic acid)
Poly(ethylene glycol terephthalate)
Poly(ethylene oxide-b-propylene oxide)

Poly(hexyl isocyanate)
Poly(methacrylic acid)
Poly(N-iso-propylacrylamide)
Poly(N-vinylpyrrolidone) (poly[N-vinylpyrrolidinone])
Poly(tetramethylene ether glycol) (Polytetrahydrofuran)
Poly(vinyl butyral)

Poly(vinylidene fluoride)
Polyacetal resin
Polybutadiene
Polyetherimide
Polymethacrylamide
Polystyrene Poly ether ether ketone (PEEK)
Poly(2,6-dimethyl-1,4-phenylene oxide)
Poly(2-hydroxyethyl methacrylate)
Poly(2-vinylpyridine)
Poly(3-octylthiophene)
Poly(4-chlorostyrene)
Poly(4-vinylpyridine)
Poly(alpha-methylstyrene)
Poly(chlorotrifluoroethylene)
Poly(dl-lactide/glycolide)
Poly(ethylene glycol) (PEG)
Poly(hexamethylene adipamide)

Poly(iso-propyl methacrylate)
Poly(methyl isopropenyl ketone)
Poly(N-methylvinylamine)
Poly(tert-butyl methacrylate)

Poly(vinyl acetate)

Poly(vinyl chloride)

Poly(vinylphosphonic acid)
Polyacrolein
Polycaprolactam
Polyethylene
Polypropylene
Polysulfone

*Figure 5*

| Herbicide Class | Common Name | Trade Name |
| --- | --- | --- |
| Dinitroanilines | Pendimethalin | Prowl, Stomp |
|  | Oryzalin | Surflan |
| Nitriles | Bromoxynil | Buctril, Merit |
| Aliphatic acids | Dalapon | Dalacide, Unipon |
| Phenoxy-benzoic acids | Dicamba | Banvel |
| Phosphonates | Glyphosate | Roundup, Range, Rodeo, Kleenup |
| Pyridines | Picloram | Tordon |
|  | Triclopyr | Garlon, Grandstand, Turflon |
| Substituted amides | Alachor | Lasso, Partner |
|  | Metolachlor | Dual, Dual II, Pennant |
|  | Propanil | Stampede, Surcopur |
|  | Pronamide | Kerb |
| Thiocarbamates | Butylate | Sutan+ |
|  | EPTC | Eptam, Eradicane |
|  | Molinate | Ordram |
|  | Triallate | Buckle, Far-Go |
| Triazine and Triazoles | Amitrol | Amitrol, Amizol |
|  | Atrazine | AAtrex, Atrazine |
|  | Cyanazine | Bladex, Fortrol |
|  | Hexazinone | Velpar |
|  | Metribuzin | Sencor, Sencoral, Sencorex |
|  | Propazine | Primatol |
|  | Simazine | Princep, Caliper 90 |
| Uracils | Bromacil | Hyvar |
|  | terbacil | Sinbar |
| Ureas | Diuron | Seduron, Direx, Karmex |
|  | fluometuron | Cotoran |
|  | Linuron | Linex, Lorox |
| Acylalanine | Metalaxyl | Ridomil, Apron |
| Analide | Carboxin | Oxatin, Vitavax |
| Benzimidazole | Benomyl | Funomyl, Benex, Benlate |
|  | Thiabendazole | Arbotect, Mertect, Storite |
| Substituted Aromatics | Chlorothalonil | Bravo, Daconil 2787, Tuffcide |
|  | Hexachlorobenzene (HCB) | No Bunt |
|  | PCNB (Quintozene) | Terraclor, Turcide |
| Dicarboximide | Iprodione | Kidan, Rovral, Chipco 26019 |
|  | Vinclozolin | Ronilan, Ornalin |
| Dinitrophenyl | Dinocap | Crotothane, Mildane |
| Dithiocarbamates | Mancozeb | Dithane, Fore, Tridex, Manzate |
|  | Maneb | Manex, Manox, Maneb 80 |
|  | Thiram | Thiram 75 WG, Tripomol |
| Guanidine | Dodine | Venturol, Melprex |
| Inorganic | Copper Sulfate | Blue Viking, Triangle Brand |
| Phthalimide | Captan | Captanex, Merpan |

*Figure 10*

| Species | Isolate No. | [SIF] ppm | % Growth Inhibition /Stimulation ( ) | | | | |
|---|---|---|---|---|---|---|---|
| | | | Propiconazole | Triadmefon | Fenarimol | Myclobutanil | Average |
| Chlorella fusca var vacuolata | 251 | 5 | 78.8 | 97.6 | 96.0 | 85.9 | 89.6 |
| Oocystis polymorpha | 1645 | 5 | 90 | - | 83.5 | 93.6 | 89 |
| Chlorella anitrata | 1798 | 5 | 96.3 | 26.5 | 56.7 | 88.8 | 67 |
| Chlorella sorokiniana | 1810 | 5 | 23.4 | 54.5 | 82.6 | 37.7 | 49.6 |
| Chlorella luteoviridis | 24 | 5 | 49.4 | 47.4 | 45.5 | - | 47.4 |
| Cylindrotheca fusiformis | 2084 | 5 | 76.0 | 13.8 | 36.1 | 53.6 | 44.9 |
| Phaeodactylum tricornutum | 640 | 5 | 82.2 | (30.6) | 34.8 | 72.9 | 39.8 |
| Porphridium aerugineum | 755 | 5 | 26.9 | 44.4 | 55.3 | - | 36.4 |
| Chlorella saccharophila | 247 | 5 | 73.5 | 49.7 | 6.8 | (17.3) | 28.2 |
| Chlorella vulgaris | 1803 | 5 | 54.9 | 9.9 | 53.1 | (11.4) | 26.6 |
| Chlorella vulgaris | 1809 | 5 | 38.6 | (37.2) | (41.1) | 27.3 | (3.1) |
| Chlorella sorokiniana | 246 | 5 | (44.3) | (41.6) | 30.8 | 20.4 | (8.7) |
| Oocystis polymorpha | 1645 | 10 | - | 76.8 | - | - | 76.8 |
| Oocystis marsonii | 287 | 10 | 19.8 | 35.1 | 48.2 | 46.4 | 37.4 |
| Chlorella vulgaris | 1809 | 10 | 42.0 | (4.9) | 41.0 | 21.3 | 24.9 |
| Euglena gracilis | 753 | 10 | 16.7 | 24.5 | 21.4 | 16.1 | 19.7 |
| Synechococcus leopoliensis | 625 | 20 | - | 86.0 | - | 87.0 | 86.5 |
| Chlorella vulgaris | X | 20 | 77.4 | 49.8 | 39.1 | 51.1 | 54.4 |
| Chlorella kessleri | 262 | 20 | 91.4 | (32.0) | 91.8 | 57.3 | 52.1 |
| Chlorella vulgaris | 1803 | 20 | 81.3 | 62.5 | 10.2 | 42.5 | 49.1 |
| Average % Inhibition | | | 54.1 | 28.0 | 44.0 | 45.5 | |

- Isolate No. indicates the environment from which the species was cultured and isolated.
- SIF= Sterile Inhibiting Fungicide

*Figure 11*

ANTIBIOFOULING METHOD AND APPARATUS FOR OPTICAL SENSORS

This application claims the benefit of U.S. Provisional Patent Application Serial No. 60/199,347 filed Apr. 25, 2000, the entire disclosure of which is incorporated herein by reference. This application is also related to, and claims the benefit of, U.S. Provisional Patent Application Serial No. 60/199,346 entitled "System and Method for Distributed Monitoring Using Remote Sensors" filed Apr. 25, 2000, the entire disclosure of which is incorporated herein by reference.

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

BACKGROUND OF THE INVENTION

1. Field of the Invention

The invention relates generally to a chemical methodology for protecting sensors from biofouling, especially those in contact with fresh water, seawater, wastewater, effluent, or high humidity environments, and in particular the invention relates to antifouling biocidal compounds and/or mixtures that are active at parts-per-million (ppm) and/or parts-per-billion (ppb) concentrations.

2. Related Art

The occurrence of biofouling is a common problem for surfaces in contact with fresh water, seawater, wastewater, effluent, or high humidity environments. Although only considered a nuisance in many instances, biofouling in aquatic sensors is detrimental to the life of the sensor and the quality of data collected by such sensors. Previously, non-mechanical antifouling methodologies have been developed for the treatment of heat exchangers, platforms, pools, ponds, ships, submarines, and even industrial plants. However, to date, no one has developed a non-mechanical, non-electrical antifouling methodology for sensors. Reference U.S. Pat. No. 5,889,209 for a mechanical antifouling apparatus for aquatic sensors.

Historically, sensors have been employed to detect the presence of analytes in biologically active media, such as oceans, lakes, streams, rivers, wastewater treatment facilities, and industrial effluent. The problem that has plagued both the manufacturers and users of the sensors is that within hours of being submerged within a biologically active media, all surfaces develop a bacterial film. This film subsequently acts as a substrate for algae growth. The net effect of the formation of bacteria and algae is sensor drift, which is an undesirable trait for long-term monitoring.

Prior non-mechanical, non-electrical, chemical-based antifouling methodologies have consisted of leachable or photocatalytic biocides (metal oxides), as described in U.S. Pat. No. 5,518,992, embedded within an inert binder, polymer, or "self-polishing copolymer" paints, as described in U.S. Pat. No. 5,717,007. U.S. Pat. No. 5,776,856 discusses the use of water-soluble matrices for water-insoluble, agrochemically active chemicals for crop treatment. U.S. Pat. Nos. 4,818,797, 6,017,561 and 5,116,407 discuss the use of quaternary ammonium compounds and amines that behave as binders and marine biocides, and work in combination with acid functional polymers. The acid groups of these polymers are blocked by the ammonium compound or monoamine group, which form an organic-solvent-soluble salt of the polymer.

Recently, U.S. Pat. No. 5,849,311 disclosed non-leaching metal based biocidal materials as well as methods of manufacture and use of such materials. Finally, U.S. Pat. Nos. 5,902,820, 5,981,561, 5,981,582, 5,998,391, and 6,004,947 all discuss methods for using synergistic admixtures of biocidal compounds to treat surfaces.

Unfortunately, the high biocide concentration levels associated with the aforementioned approaches causes the biocides to interfere with many sensors, thus making such technologies inapplicable to sensor protection. This is especially true for optical sensors, or "optrodes", in which chemical reactions between a sensor and some biocides can cause sensor failure. A secondary concern is the leaching of the biocide from a containing matrix, which has also been shown to significantly affect the performance of optrodes.

Some have sought to rectify such shortcomings through software-oriented approaches. For example, some in the prior art periodically recalibrate optrode or other sensor inputs to ensure accurate readings. Others in the prior art use software to control application of periodic, relatively high energy electricity to a sensor, thereby retarding biofouling.

SUMMARY OF THE INVENTION

The present invention provides a non-electrical, non-mechanical, and non-software oriented methodology for protecting sensors, with specific applicability to retarding or eliminating optrode biofouling. The use of optrodes for the determination of many different analytes in a number of environments is well documented. One commonality between all optrodes is that they exhibit phenomena such as temperature sensitivities, cross-sensitivities to other analytes, pH dependencies, and support/solvent interactions. Support/solvent interactions are interactions that develop as a result of embedding luminescent probes in a support matrix.

BRIEF DESCRIPTION OF THE FIGURES

FIG. 1 illustrates Halobenzonitriles, one of which, chlorothalonil, represents the preferred biocide for the protection of optrodes. This biocide has been shown to be effective even at ppb concentrations.

FIG. 3 illustrates Biocides, all of which represent alternatives for optrode protection.

FIG. 4 lists alternative anti-biofouling agents.

FIG. 5 is a partial list of potential host matrix candidates.

FIG. 10 shows a list of alternative agents for the protection of optrodes, including common and trade names.

FIG. 11 shows experimental evidence as to the effectiveness of azoles, an alternative preferred embodiment.

DETAILED DESCRIPTION

The present invention provides a non-electrical, non-mechanical, and non-software oriented methodology for protecting sensors, with specific applicability retarding or eliminating optrode biofouling. The use of optrodes for the determination of many different analytes in a number of environments is well documented. One commonality between all optrodes is that they exhibit phenomena such as temperature sensitivities, cross-sensitivities to other analytes, pH dependencies, and support/solvent interactions. Support/solvent interactions are interactions that develop as a result of embedding luminescent probes in a support matrix.

FIG. 5 is a list of supports applicable to the embodiments of the present invention set forth in this disclosure. The list presented in FIG. 5 is not intended to limit the present invention to these supports, as additional supports will be apparent to one skilled in the art depending on the specific sensor type and the environment in which the sensor will be deployed.

Several supports have been examined and all exhibit signs of interactions, including interactions with biocides. Of particular importance is a body of evidence that shows unambiguously that molecular weight differences lead not only to solvatochromism (a shift in the emission spectra due to a change in the permittivity of the luminescent probe's local environment), but also a shift in the lifetime of the excited state. This is important as high molecular weight biocides can result in an apparent molecular weight decrease as measured by a probe, thus affecting an optrode's performance. For example, the addition of a biocide may serve to decrease the lifetime of a molecular probe, and if the lifetime is too short to allow diffusion controlled quenching to occur, the result can be an ineffective sensor.

Figure 2:
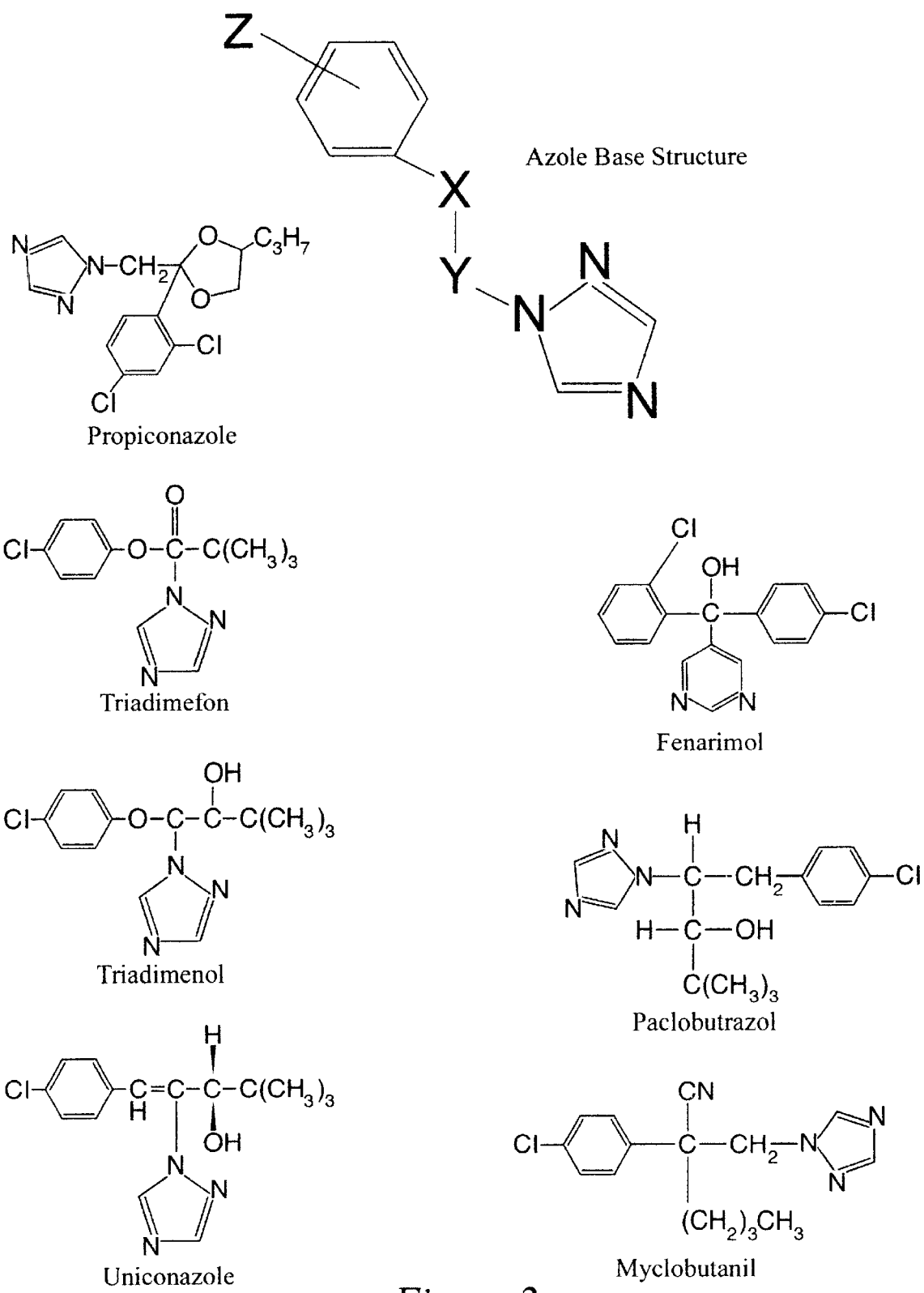
FIG. 2 illustrates Azoles, most of which have been shown to be effective even at ppm concentrations and represent a alternative preferred biocides for optrode protection.
Figure 6:
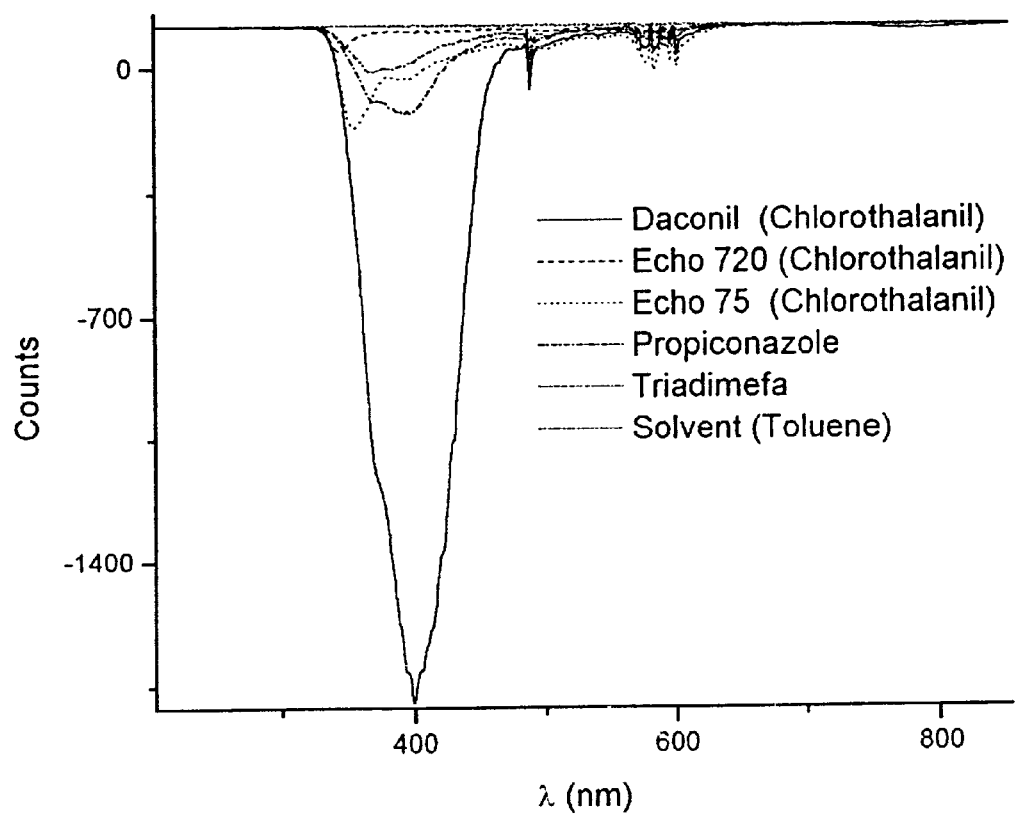
FIG. 6 is a graphical representation of the visible absorption spectrum for five preferred biocides.
Figure 7:
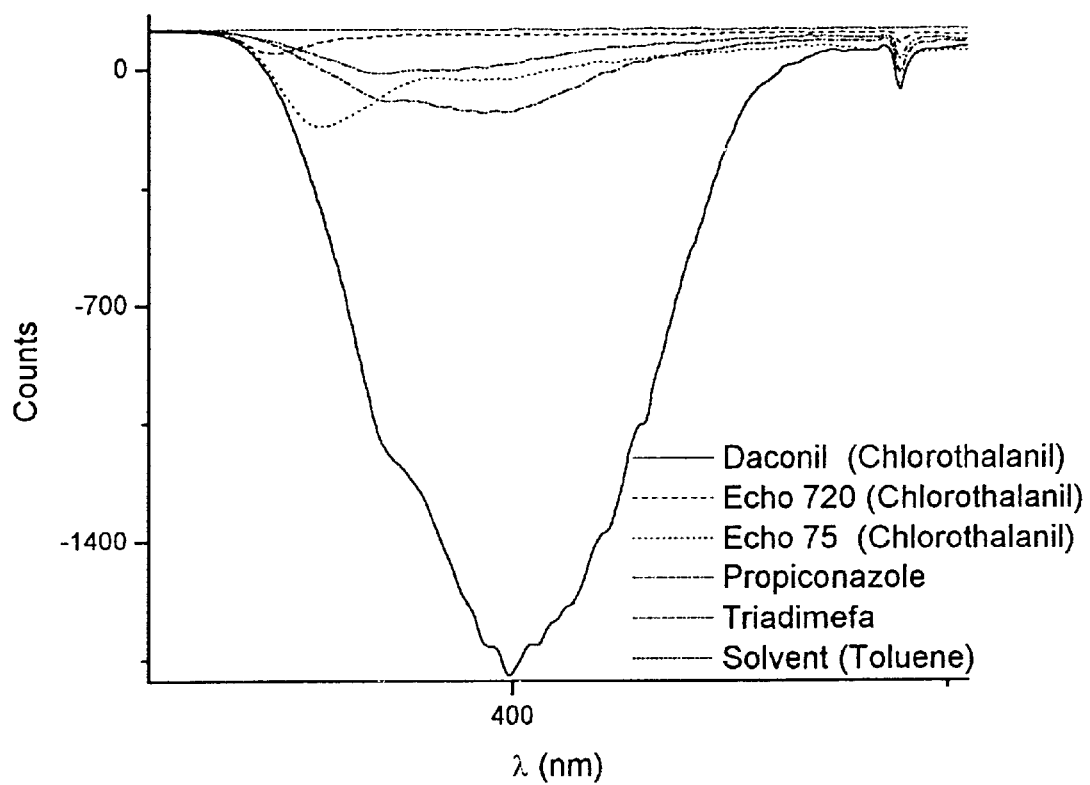
FIG. 7 is a graphical representation of the visible absorption spectrum within the excitation region of typical optrodes.
Figure 8:
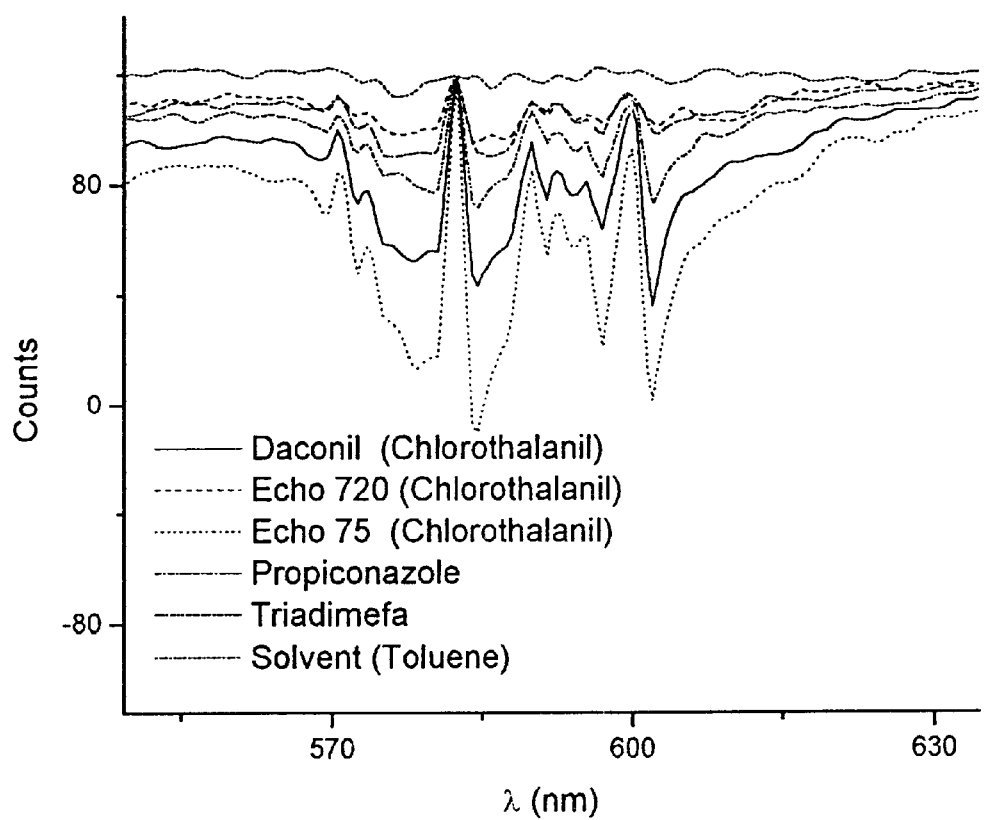
FIG. 8 shows visible absorption spectrum within the emission region of an optrode.
Figure 9:
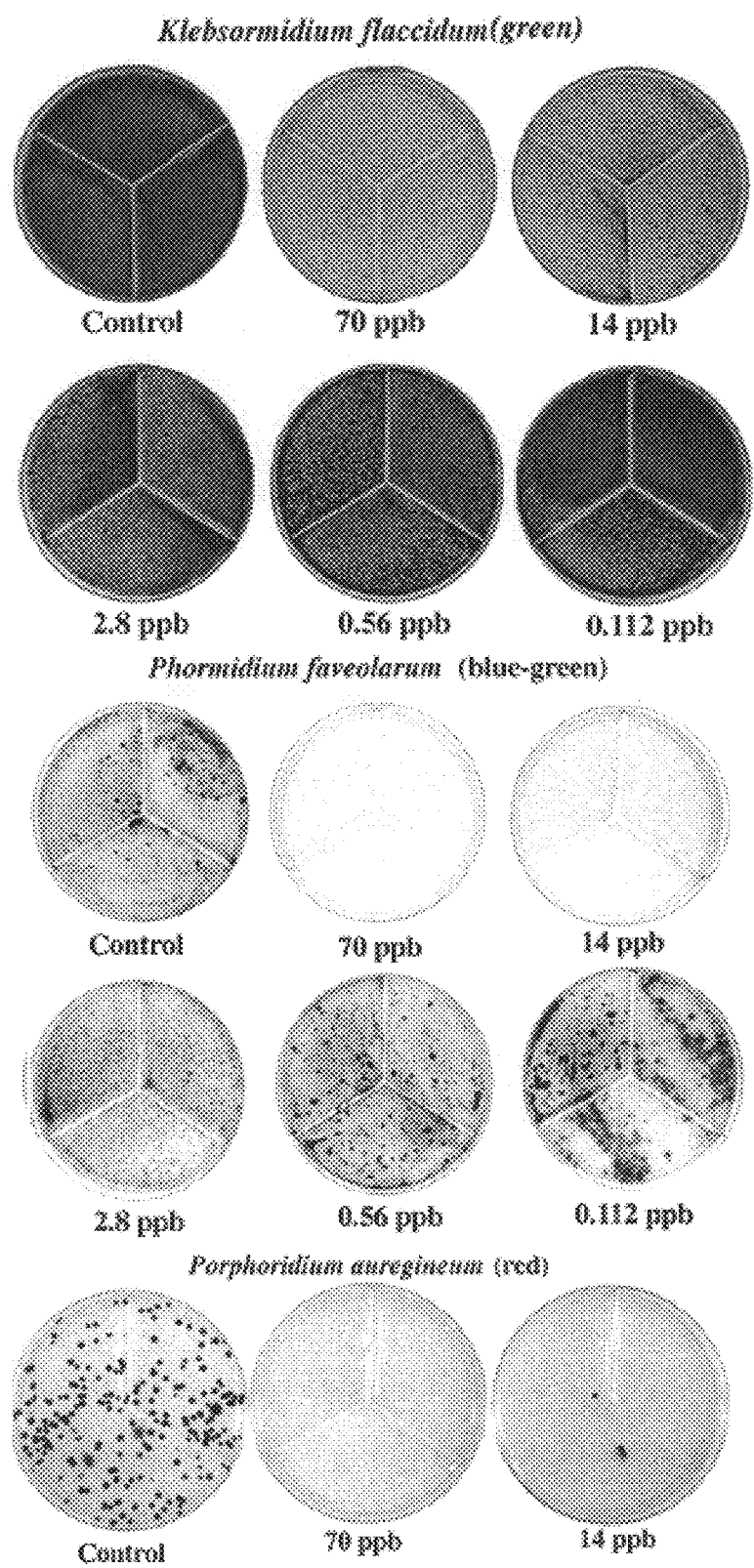
FIG. 9 shows a photograph illustrating experimental evidence of the effectiveness of the preferred embodiment at 70 ppb toward the growth of green, blue-green and red algae.

FIG. 7 is a graphical representation of the visible absorption spectrum within the excitation region of typical optrodes. The excitation wavelength for the optrode in this particular case is 470 nm, which is outside the absorption window for all compounds except daconil. It is suspected that the carrier for chlorothalonil within daconil is responsible for the broad absorption shown. Reference the absorptions of echo 720 and echo 75, both of which contain chlorothalonil as the active ingredient.

FIG. 8 shows visible absorption spectrum within the emission region of an optrode. The emission wavelength for the optrode in this particular case is 610 nm. Note that all compounds exhibit very little absorption in this wavelength region, which is critical to the operation of many optrodes.

As is apparent from FIGS. 7 and 8, the solution to the high concentration problem is to use biocides that are effective at low levels such that the optrode is not sensitive to their presence in a support matrix. At low levels, it is believed that performance of intensity based optrodes is enhanced by their electronic structure, which allows them to behave as single $O_2$ scrubbers. This behavior can prolong the life of the sensor through a mechanism other than the inhibition of biofouling. Additionally, it is believed that many of the molecular probes used in optrodes behave synergistically with some of these low-level biocides, thus enhancing the efficacy of the biocide.

The invention in its preferred embodiment employs cholorothalonil (a biocide) at sub ppm concentrations and a metal-ligand charge transfer compound, ruthenium(II) tris (4,7 diphenyl-1,10-phenanthroline) embedded within a free radical polymerized, UV-initiated, copolymer. Other polymerization and matrix isolation mechanisms can also be used, including, but not limited to, emulsion polymerization, condensation polymerization, and living anionic polymerization. FIG. 9 includes several photographs providing experimental evidence of the effectiveness of a preferred embodiment of the present invention toward the growth of green, blue-green and red algae utilizing the biocide described above at concentrations in the seventy parts per billion range. Alternative embodiments include, but are not limited to, the use of biocides such as listed in FIG. 4 and FIG. 10 and of polymers such as listed in FIG. 5.

While the invention has been particularly shown and described with reference to a preferred embodiment thereof, it will be understood by those skilled in the art that various changes in form and details may be made therein without departing from the spirit and scope of the invention.

We claim as our invention:

1. An antibiofouling material, in which one or more biocides of a concentration not exceeding ten parts per million and one or more charge transfer compounds are embedded within a copolymer host matrix.

2. The material of claim 1, wherein the biocide employed includes one or more of the following: Halobenzonitriles; Azoles; atrazine; diuron; and simazine.

3. An antibiofouling material, comprised of chlorotalonil at a concentration below one part per million and ruthenium (II) tris (4,7 diphenyl-1, 10 phenanthroline) embedded within a free radical polymerized, UV-initiated copolymer host matrix.

4. An antibiofouling material production process, comprising the steps of:

selecting one or more biocides whose concentration does not exceed ten parts per million;

selecting one or more charge transfer compounds; and, embedding said biocides and said charge transfer compounds in a copolymer host matrix.

5. The material of claim 2, wherein said Halobenzonitriles comprise one or more biocides from a group containing chlorothalonil, chloroxynil, bromoxynil, ioxynil, and dichlobenil.

6. The material of claim 2, wherein said Azoles comprise one or more biocides from a group containing propiconazole, fenarimol, triadimefon, triadimenol, paclobutrazol, uniconazole, and myclobutanil.

7. The antibiofouling material of claim 1, wherein the material is a coating on one or more surfaces of a sensor apparatus.

* * * * *